United States Patent [19]

Steiner et al.

[11] 4,025,523
[45] May 24, 1977

[54] CYCLIC TETRA-OXYETHYLENE COMPLEXES WITH IONIC COMPOUNDS

[75] Inventors: Edwin C. Steiner, Midland, Mich.; Robert A. Newton; F. Peter Boer, both of Lake Jackson, Tex.

[73] Assignee: The Dow Chemical Company, Midland, Mich.

[22] Filed: May 24, 1976

[21] Appl. No.: 689,003

Related U.S. Application Data

[63] Continuation of Ser. No. 460,866, April 15, 1974, abandoned.

[52] U.S. Cl. .............................. 260/297 R; 423/1; 423/497; 423/499; 260/338
[51] Int. Cl.² ........................................ C07D 403/02
[58] Field of Search ..................... 260/338, 297 R

[56] References Cited

UNITED STATES PATENTS 3,760,005   9/1973   Exner et al. ................... 260/615 B

OTHER PUBLICATIONS

Down et al. (I), Chemical Abstracts, vol. 52, col. 47f, (1958).
Down et al. (II), Journ. Chem. Soc., 1959, pp. 3767–3773.
Frensdorff, J. Am. Chem. Soc. vol. 93, pp. 600–606, (1971).
Chemical Abstracts (I), vol. 52, cols. 5038 to 5039, (1958).
Chemical Abstracts II, Sixth Collective Index, p. 11524s.
Chemical Abstracts III, vol. 74, Subject Index p. 3526S, (1971).
Chemical Abstracts IV, vol. 74, abst. No. 68434c, (1971).

*Primary Examiner*—John D. Randolph
*Attorney, Agent, or Firm*—David H. Fifield

[57] ABSTRACT

Novel complexes between (a) a compound of the formula

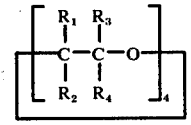

where $R_1$, $R_2$, $R_3$ and $R_4$ are independently H or $C_1$–$C_3$ alkyl; and (b), salts of one of the cations Li, Na, K, Rb, Mg, Ca, Sr, Mn (II), Mn (III), Fe (II), Fe (III), Cu (I), Cu (II), Ag (I), Zn (II), Sn (II), Au (I), Au (II), Hg (I), Hg (II), Ni (I), Ni (II), Co (II), Co (III), hydronium, ammonium alkylammonium and pyridinium; optionally with solvent molecules in the crystal lattice, which complexes are useful as sources of highly pure salts and as soluble sources of certain inorganic reagents, e.g., $KMnO_4$, $NaNO_2$, NaSCN, etc., in hydrocarbon systems. For example, a 1:2 complex of sodium chloride and $[CH_2CH_2O]_4$ is formed with 5 molecules of water per sodium cation in the crystal lattice of the complex.

2 Claims, No Drawings

CYCLIC TETRA-OXYETHYLENE COMPLEXES WITH IONIC COMPOUNDS

CROSS-REFERENCE TO RELATED APPLICATION

This is a continuation, of application Ser. No. 460,866 filed Apr. 15, 1974 now abandoned.

BACKGROUND OF THE INVENTION

Field of the Invention

The invention relates to novel complexes of cyclic polyethers with ionic compounds.

The cyclic oxyethylene tetramer, and complexes thereof, are toxic and should be handled with due care. Inhalation and skin contact should be avoided.

Description of the Prior Art

The cyclic tetramer of ethylene oxide is described by Stewart et al. in the British Patent 785,229. A sodium-potassium alloy is said to form a deep-blue solution with a cyclic tetramer of propylene oxide, of the formula

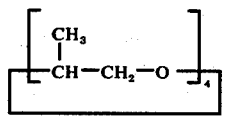

by Down et. al. in *J. Chem. Soc.* (London) 3767 (1959). Pederson, in U.S. Pat. No. 3,562,295 described complexes of alkali and alkaline earth metal salts with cyclic oligomers of oxyethylene or oxypropylene units which contain from 5 to 10 of the oxyalkylene units. Pederson, in U.S. Pat. No. 3,686,225, describes the preparation of complexes between lithium or sodium bromide and a cyclic polyether represented by the formula

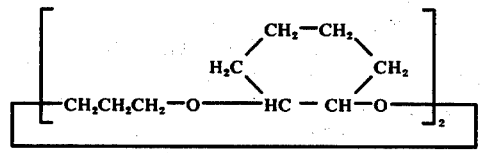

as well as other complexes with higher oligomers also bearing benzene or cyclohexane rings.

SUMMARY OF THE INVENTION

Disclosed is a composition of matter comprising a complex between (a) a cyclic tetramer represented by the formula

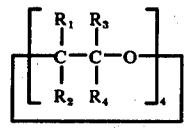

wherein $R_1$, $R_2$, $R_3$ and $R_4$ are independently hydrogen or alkyl of from 1 to about 3 carbon atoms; and (b) a salt of one of the cations selected from the group of cations consisting of: lithium, sodium, potassium, rubidium, magnesium, calcium, strontium, manganese (II), manganese (III), iron (II), iron (III), copper (I), copper (II), silver (I), zinc (II), tin (II), gold (I), gold (II), mercury (I), mercury (II), nickel (I), nickel (II), cobalt (II), cobalt (III), hydronium, ammonium, pyridinium and monoalkyl ammonium, wherein the alkyl group comprises 1 to about 20 carbon atoms.

The complex contains the neutralizing anion of the salt (hereinafter gegen ion from the German for "counter ion") and may also contain water or other solvent molecules in the crystal lattice.

The composition is useful as a source of the high purity salt, available when the complex is broken. The complexes are broken by hot benzene. It is also useful as a soluble source of inorganic reagents which are otherwise insoluble in hydrocarbon media, for example, potassium permanganate, sodium nitrite, sodium thiocyanate and the like. Some of the invention compositions may also be used to selectively extract certain ions from solution.

The invention compositions, amorphous or crystalline solids, are prepared by adding the chosen salt to enough water to dissolve it. The resulting solution is in turn contacted with the chosen cyclic tetramer to give the novel complex. Where anhydrous complexes are desired, the hydrated complex is dried with a nitrogen stream, crystals ae allowed to grow into an organic solvent phase or the reagents are contacted in an organic solvent in which the resultant complex is insoluble.

DETAILED DESCRIPTION OF THE INVENTION
CYCLIC TETRAMERS

The cyclic tetraoxyalkylene compounds employed in preparing the invention composition are represented by the formula

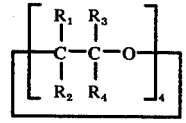

wherein $R_1$, $R_2$, $R_3$ and $R_4$ are as described; compounds where $R_2$, $R_3$ and $R_4$ are hydrogen are preferred in the invention while the compound wherein $R_1$, $R_2$, $R_3$ and $R_4$ are all hydrogen is especially preferred.

The cyclic tetraoxyethylene compound may be prepared by reacting the $\alpha,\omega$-disodium salt of diethylene glycol with 2,2'-dichlorodiethyl ether. To prepare substituted derivatives where $R_1$, $R_2$, $R_3$ and $R_4$ are not all hydrogen, suitably substituted reactants are employed. For example, reactants represented by the formulas

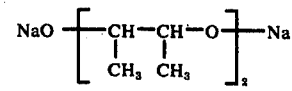

and

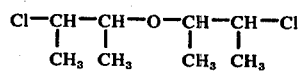

will be combined to give a cyclic compound represented by the formula

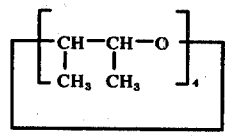

Other derivatives of the cyclic tetramer used in preparing the invention composition may be prepared in a like manner.

COMPLEXED IONS

The cation to be complexed by the cyclic tetramer will be supplied by a salt of that cation. For example, the sodium ion may be supplied by sodium bromide, sodium iodide, sodium thiocyanate or similar sodium salts, with the gegen ion of said salt then becoming the gegen ion associated with the sodium cation in the resulting complex.

Ions which are suitably complexed with the cyclic tetramers are lithium, sodium, potassium, rubidium, magnesium, calcium, strontium, manganese (II), manganese (III), iron (II), iron (III), copper (I), copper (II), silver (I), zinc (II), tin (II), gold (I), gold (II), mercury (I), mercury (II), nickel (I), nickel (II), cobalt (II), cobalt (III), hydronium, ammonium, monoalkyl ammonium the alkyl portion of which comprises from one to about 20 carbon atoms, and pyridinium. Cations preferably complexed are lithium, sodium, potassium, rubidium, magnesium, calcium, strontium, manganese (II), iron (III), copper (II), silver (I), zinc (II), tin (II), hydronium, ammonium and pyridinium.

X-ray diffraction analysis has shown the cations are most commonly "held" by the oxygen atoms of cyclic tetramer molecules while the gegen ions are either closely or distantly associated with their cations in the normally crystalline lattice of the complex. However, complexes can form where the cation is mostly closely associated with molecules of a solvent, for example water, and the oxygen atoms of the cyclic tetramer are closely associated with atoms of the solvent molecules. While the gegen ion of the complex is normally the gegen ion of the salt supplying the complexed cation, where the complex is formed from an aqueous solution of an acid, the gegen ion of the complex will be the anion of the acid while a hydronium ion is the cation complexed by the cyclic tetramer.

The anions found as the gegen ions of the abovementioned complexes may be any of the common anions, for example, chloride, bromide, iodide, permanganate, nitrate, nitrite, perchlorate, thiocyanate, hydroxide, phenate, acrylate, methacrylate and the like. The anions are supplied in most instances by the salt of the cation which is complexed. In certain instances, however, the anion may be formed in situ as when sodium bromide and liquid bromine are added to the tetraoxyethylene cyclomer to form a complex of the cyclomer and the sodium cation with the associated tribromide gegen ion residing in the crystal lattice.

SOLVENTS

In addition to the salt and cyclic tetramer, solvent molecules may also be found in the crystal lattice of the complexes when they are formed in the presence of solvents. In most such instances, a composition free of solvent may be prepared by drying the substance with a stream of dry nitrogen gas or by other conventional drying methods. For example, phenol, water and methacrylic acid molecules have been observed to be present in the crystal lattices of some complexes prepared in solutions thereof.

RECOVERY OF PURE SALTS

To produce salts of high purity which may be used when purity is of importance, i.e., analytical work, etc., the salt:cyclomer complexes which are prepared according to the invention are either heated, treated with solvents which extract the cyclomer and cause the salt to precipitate or contacted with materials which will preferentially complex either the cyclomer or the salt.

For example, the sodium chloride:tetramer complex was broken by heating to about 150° C. whereupon the sodium chloride precipitated, and was filtered, washed and recovered. The calcium chloride: tetramer complex was broken by contacting with liquid ammonia whereupon a calcium chloride:ammonia complex precipitated, was separated from the liquid ammonia and tetramer mix and the pure calcium chloride was obtained by heating to drive off the ammonia.

In other instances the salt-cyclomer complex may be broken and the salt recovered by conventional solvent extraction techniques. Benzene, toluene, methylene chloride and the like may be used to extract the cyclomer from aqueous solutions of the complex with subsequent evaporation of the aqueous layer to recover the pure salt. Such solvents may also be contacted with the salt:cyclomer complex alone and heated causing the salt to precipitate and the cyclomer to be left in the solvent. The salt may then be filtered for recovery. Other means for recovering the pure salts once a salt:cyclomer complex has been prepared will be apparent to those skilled in the art.

SPECIFIC EMBODIMENTS OF THE INVENTION

Crystalline complexes between cyclic tetraoxyethylene of the formula $\mathrm{[CH_2CH_2O]_4}$ (hereinafter EOc4) and alkali metal salts, alkaline earth metal salts, transition metal salts, nitrogen base salts and hydronium ions and the gegen ions (from Brönsted acids in aqueous solutions), were prepared by contacting the cyclic tetraoxyethylene with the salt whose cation was to be complexed, in the presence of water or another solvent. Complexation in some instances was encouraged by warming the salt slightly with a small quantity of water and the cyclic tetramer. On cooling, crystals of the complex formed. They were filtered and washed with a proper solvent and recrystallized to obtain the complex in pure form. In other instances the complexes were prepared by merely warming the salt with the chosen cyclic tetramer.

Polyhalide salt complexes may be formed by bubbling a halogen gas, for example bromine, through a halide salt-EOc4 mixture. Means for preparing hydronium and pyridinium salt complexes are described in more specific examples below.

Crystals of the complexed materials were found to be birefringent and appeared as bright and often highly colored crystals under a polarizing microscope. In cases where the uncomplexed salt was also birefringent, complexation was easily noted by change in the crystalline form under microscopic observation. Polarizing microscopy was also employed to evaluate solvent systems for recrystallization and for selecting crystals to be used for the X-ray diffraction analysis that was made of some of the crystal structures. Infrared spectroscopy was used for water analysis in some instances. Standard titrimetric methods were ordinarily used for determination of cation, gegen ion, acid, base and water content of the complexes.

In cases where solvent incorporation in the crystal lattice was possible, vapor phase chromatography or nuclear magnetic resonance (NMR) analysis was used. All complexes are expressed in terms of molar ratios.

The examples shown below demonstrate representative means for preparing the invention compositions. The table illustrates those complexes which have been prepared.

was found to be the 1:2 sodium chloride:EOc4 complex in essentially anhydrous form.

The 1:2 sodium chloride:EOc4 pentahydrate complex was broken by heating to about 150° C. A sample

EOc4 COMPLEXES PREPARED

| Example No. | Type of Salt in Complex | | Molar Ratio of Complex's Components | | | Comments |
|---|---|---|---|---|---|---|
| | Cation | Gegen ion | Moles of Salt | Moles of EOc4 | Moles and Type of Solvent | |
| 1 | Li$^+$ | Br$^-$ | 1 | 1 | None | a,c |
| 2 | " | " | 1 | 1 | 2(H$_2$O) | a,c |
| 3 | Na$^+$ | Cl$^-$ | 1 | 2 | None | a |
| 4 | " | " | 1 | 2 | 5(H$_2$O) | a,c Complex broken on heating to ca.150° C. |
| 5 | " | Br$^-$ | 1 | 2 | 5(H$_2$O) | c Isomorphous with Ex. 4 complex |
| 6 | " | I$^-$ | 1 | 2 | 5(H$_2$O) | c Isomorphous with Ex. 4 complex |
| 7 | " | OH$^-$ | 1 | 2 | None | a |
| 8 | " | " | 1 | 2 | 8(H$_2$O) | a,c |
| 9 | " | NO$_3^-$ | 1 | 2 | None | a |
| 10 | " | CH$_2$=CCH$_3$COO$^-$ | 1 | 2 | None | a |
| 11 | " | " | 1 | 2 | 5(H$_2$O) | a |
| 12 | " | " | 1 | 2 | 2(CH$_2$=CCH$_3$COOH) | a |
| 13 | " | $\phi$-O$^-$ | 1 | 2 | None | a |
| 14 | " | " | 1 | 2 | 4(H$_2$O) | a |
| 15 | " | " | 1 | 2 | 2($\phi$-OH) | a |
| 16 | K$^+$ | Cl$^-$ | 1 | 2 | 5(H$_2$O) | c Isomorphous with Ex. 4 complex |
| 17 | " | Br$^-$ | 1 | 2 | 5(H$_2$O) | c Isomorphous with Ex. 4 complex |
| 18 | Rb$^+$ | Cl$^-$ | 1 | 2 | 5(H$_2$O) | c Isomorphous with Ex. 4 complex |
| 19 | Na$^+$ | I$_3^-$ | 1 | 2 | None | c Quantitative yield with 1:2 stoichiometry |
| 20 | Na$^+$ | Br$_3^-$ | 1 | 2 | None | c Isomorphous with Ex. 19 complex |
| 21 | Li$^+$ | " | [1] | [2] | None | d Colorless ppt. formed on contacting LiBr, Br$_2$ and EOc4 |
| 22 | Mg$^{++}$ | Cl$^-$ | 1 | 1 | 6(H$_2$O) | a,c |
| 23 | Ca$^{++}$ | " | 1 | 1 | 8(H$_2$O) | a,c |
| 24 | Sr$^{++}$ | " | 1 | 1 | 4(H$_2$O) | a |
| 25 | " | Cl$^-$ | 1 | 1 | 10(H$_2$O) | a Unstable and tends to lose water |
| 26 | Mn$^{++}$ | " | 1 | 1 | [X(H$_2$O)] | a,c,f Analysis for water inconclusive |
| 27 | " | " | 2 | 1 | [X(H$_2$O)] | a,c,f Analysis for water inconclusive |
| 28 | Cu$^{++}$ | " | 1 | 1 | None | c |
| 29 | Ag$^+$ | NO$_3^-$ | — | — | — | d No analysis, colorless crystalline complexes observed |
| 30 | " | ClO$_4^-$ | — | — | — | d No analysis, colorless crystalline complexes observed |
| 31 | Zn$^{++}$ | Br$^-$ | 1 | 1 | None | a,b |
| 32 | Fe$^{+++}$ | Cl$^-$ | 1 | 1 | None | c,e,f |
| 33 | " | " | 1 | 1 | 2(H$_2$O) | c,e,g |
| 34 | " | " | 5 | 2 | 4(1,2-bis(methoxy)ethane) | c,e,f |
| 35 | H$_3$O$^+$ | Br$^-$ | [1] | [1] | [½(H$_2$O)] | a Unstable, tentative structure, colorless crystals |
| 36 | " | BF$_4^-$ | — | — | — | d No reliable analysis, colorless crystalline complex observed |
| 37 | H$_3$O$^+$ | SbF$_6^-$ | 1 | 2 | — | a,f Analysis for water (shown as part of cation), EOc4 only organic molecule |
| 38 | NH$_4^+$ | Br$^-$ | 2 | 1 | None | a,c |
| 39 | " | I$^-$ | — | — | — | d Structure not defined, colorless crystals |
| 40 | " | —SCN$^-$ | 1 | 1 | None | a (Thiocyanate gegen ion) |
| 41 | C$_5$H$_5$NH$^+$ | Br$^-$ | 1 | 2 | None | a (Pyridinium cation) |
| 42 | " | Cl$^-$ | 1 | 2 | None | a,c Isomorphous with Ex. 41 complex |
| 43 | Sn$^{++}$ | Cl$^-$ | — | — | — | d Structure not defined, colorless crystals |

Notes:
a. Titrimetric Analysis
b. Nuclear Magnetic Resonance Analysis
c. X-Ray Diffraction Analysis
d. No Analysis Performed, Complex Observed Under Polarizing Microscope
e. Special Analytical Procedure for Iron (III) Complexes
f. Vapor Phase Chromatographic Analysis for Solvent Molecules in Complex
g. Infrared Analysis for Water
—: Signifies undefined stoichiometry; [ ]or X: signify presence but quantity uncertain

EXAMPLES 3 AND 4

Sodium:EOc4 Complexes

When 17.6 g. (0.10 mole) of EOc4 were added to a solution of 5.85 g. (0.10 mole) of sodium chloride and 50 ml. water, a precipitate was immediately formed. The precipitate was recrystallized from the mother liquor to give 18.2 g. of platelets which were then dried in a nitrogen stream. The platelets were found to be a 1:2 complex of sodium chloride and EOc4, pentahydrate. When dried overnight at room temperature and 0.001 torr. pressure, a white powder was formed which of the complex was dissolved in a minimum of warm water and heated to evaporate excess water. When the temperature of the liquid reached 150° C., crystals formed and were filtered off to give a quantitative yield of pure sodium chloride. Complexes of other alkali metal halides, nitrates and phenates were similarly prepared.

EXAMPLES 7 AND 8

Sodium Hydroxide Complexes

A mixture of 4.0 g. (0.100 mole) of sodium hydroxide, 18 g. (1 mole) of water and 27.4 g. (0.156 mole) EOc4 was warmed with 35 ml. of 1,2-bis(methoxy)- ethane to effect solution of the solids and the mixture was then cooled to room temperature. Upon cooling to 0° C., crystals formed, were isolated and pressed dry. Drying caused loss of water and prevented exact determination of crystal stoichiometry. When damp crystals were analyzed, they were found to be approximately 1:2 sodium hydroxide:EOc4 complexes with 8 water molecules in the crystal lattice.

When the hydrated crystals were dried with nitrogen, an anhydrous 1:2 sodium hydroxide:EOc4 complex resulted and was identified.

EXAMPLES 10–12

Sodium Methacrylate Complexes

To 13 g. of boiling acetonitrile containing 11.5 g. (0.065 mole) of EOc4 were added 3.24 g. (0.030 mole) of sodium methacrylate and enough water (3 g.) to cause complete dissolution of the solids. The solution was then cooled to about 0° C. and the crystals formed were filtered and dried in the air overnight. The crystals were found to be the pentahydrate of the 1:2 complex of sodium methacrylate and EOc4. Further drying with a stream of dry nitrogen caused the crystals to lose water to form the anhydrous 1:2 sodium methacrylate:EOc4 complex.

A sodium methacrylate:EOc4 complex was also prepared from a methacrylic acid medium. A solution of 17.6 g. (0.100 mole) of EOc4 and 8.7 g. (0.101 mole) of methacrylic acid in 30 g. of ethyl acetate was prepared and warmed and 6.0 g. (0.056 mole) of sodium methacrylate was dissolved therein. The solution was filtered, cooled and the resultant crystals were isolated. These crystals were washed with 5% solution of methacrylic acid in ethyl acetate and dried with a nitrogen stream. Crystals were analyzed by adding a known excess of hydrochloric acid and then titrating for excess hydrochloric acid and total carboxylic acid. They were found to be a 1:2 sodium methacrylate:EOc4 complex which contained, in the crystal lattice, two molecules of methacrylic acid per molecule of sodium methacrylate.

EXAMPLE 19

Alkali Metal Trihalide Complexes

To an aqueous solution of equimolar amounts of sodium iodide and iodine was added EOc4 and immediately a quantitative amount of sodium triiodide:EOc4 1:2 complex formed as a dark brown precipitate. The precipitate was of very low water solubility but was highly soluble in organic solvents like methylene chloride, chloroform, nitromethane, ethyl acetate and various ethers. It was only sparingly soluble in methanol and ethanol and essentially insoluble in hexane and carbon tetrachloride. Other alkali metal trihalide:EOc4 complexes were similarly formed.

EXAMPLE 22

Magnesium Chloride Complex

Warming 2.03 g. (0.010 mole) of magnesium chloride hexahydrate with 3.52 g. (0.020 mole) of EOc4 caused dissolution of the salt and upon cooling, crystals were formed. The crystals were washed with ether and air-dried to form a granular, nonhygroscopic solid which was found to be the 1:1 magnesium chloride:EOc4 hexahydrate complex. Similarly, other alkaline earth salt complexes were formed, sometimes by first dissolving the salt in a small quantity of water.

EXAMPLES 26 AND 27

Manganese (II) Chloride Complexes

Equimolar quantities of manganous chloride and EOc4 were contacted and recrystallization from methanol yielded pale green needle-like crystals. Analysis showed the crystals to be a 1:1 manganous chloride:EOc4 complex.

Evaporation of aqueous solutions of manganous chloride and EOc4 yielded crystals which X-ray powder diffraction indicated were 2:1 and 1:1 complexes of manganous chloride:EOc4 and appeared to contain water of hydration in undetermined proportions.

EXAMPLE 28

Copper (II) Chloride Complex

A mixture of 17.1 g. (0.100 mole) of cupric chloride, 19.3 g. (0.110 mole) of EOc4 and 10 ml. of water was warmed with just enough 2-propanol to cause dissolution at the boiling point. When cooled, the solution yielded 28 g. of yellow crystals. Analysis showed the crystals to be a 1:1 cupric chloride:EOc4 complex with no molecules of solvent in the crystal lattice. Silver, zinc and tin salt complexes were also formed by contacting EOc4 with solutions thereof.

EXAMPLES 32–34

Iron (III) Chloride Complexes

Ferric chloride, 8.6 g. (0.053 mole) was dissolved in 75 ml. of anhydrous ether. The solution was filtered and 9.0 g. (0.051 mole) of EOc4 was then added to the filtrate, an orange precipitate being immediately formed. The precipitate was filtered off, dried in a nitrogen stream and 15.8 g. of the precipitate was recovered as an amorphous orange powder. The material was found to be a 1:1 ferric chloride:EOc4 complex. Vapor phase chromatography showed that there were no ether molecules incorporated in the complex.

On exposure to moist air, the above described orange powder was soon converted to bright yellow crystals. The weight gain of the sample closely approximated the theoretical gain necessary to produce the dihydrate of the 1:1 ferric chloride: EOC4 complex. Chloride analysis of the crystals showed a chloride content which varied in proportion to the weight gain attributed to water indicating that water was not reacting to give off hydrochloric acid.

In another instance, 1.62 g. (0.10 mole) of ferric chloride and 1.76 g. (0.010 mole) of EOc4 were warmed in a solution of 10 ml. of 1,2-bis(methoxy)-ethane and 3.7 ml. of ether to dissolve the solids. As the solution cooled, more ether was slowly added and crystals formed. After washing with ether and drying with nitrogen, 1.88 g. of crystals was recovered. Analysis showed the product to be a 5:2 ferric chloride:EOc4 complex with four molecules of 1,2-bis(methoxy)-ethane present in the crystal lattice for every five ferric chloride molecules.

EXAMPLES 35–37

Hydronium Ion Complexes

Attempts to prepare a complex of anhydrous hydrogen bromide and EOc4 yielded only minor amounts of crystals. It was found that a complex was readily formed from an aqueous hydrogen bromide solution and further investigation revealed that earlier crystals were formed due to the presence of water in the "anhydrous" hydrogen bromide, indicating that water was required for complex formation. The implication is that a hydronium cation is formed and complexed by the EOc4 molecule. It will be understood, however, that whether or not the hydronium cation actually exists in the complex, the term "hydronium cation," as used herein, signifies the cation formed in an aqueous solution of a Brönsted acid.

The crystals of the aqueous hydrogen bromide:EOc4 complex were found to be very unstable and liquefied readily on loss of hydrogen bromide.

Well-formed crystals were made by combining an ether solution of equimolar quantities of hydrogen fluoride and boron trifluoride with EOc4 and water in ethyl acetate. The crystals were also too unstable to obtain reliable analysis or X-ray crystal structure but a complex of the hydronium cation and and EOc4 was indicated.

The existence of a hydronium cartion:EOc4 complexes was substantiated by adding 4.4 g. (0.020 mole) of antimony pentafluoride to an ether solution of 0.47 g. (0.023 mole) of hydrogen fluoride and then adding 0.38 g. (0.021 mole) of water to form a voluminous precipitate. To this mixture was then added 8.1 g. (0.046 mole) of EOc4 resulting in the formation of a precipitate which was transformed to a pinkish powder by trituration under ether. The pink powder was isolated and recrystallized from a 3:2 mixture of ethyl acetate and nitromethane yielding well-formed crystals which were fairly insoluble in water. Analysis showed the crystals to be a 1:2 hexafluoroantimonic acid ($HSbF_6$):EOc4 complex with one molecule of water in the crystal lattice for each $HSbF_6$ moiety. Vapor phase chromatography showed EOc4 to be the only organic molecule in the complex.

EXAMPLE 38

Ammonium Bromide Complex

These complexes were prepared by dissolving substantially equimolar amounts of ammonium bromide and EOc4 in a minimum of water at room temperature. The water was evaporated under vacuum at room temperature, solid crystals recovered and air dried. Analysis showed a 2:1 ammonium bromide:EOc4 complex. Treatment of the crystals with methanol and other solvents caused the complex to be broken. An ammonium iodide complex of undefined structure was similarly prepared. It was a colorless crystalline material.

EXAMPLE 40

Ammonium Thiocyanate Complex

Ammonium thiocyanate, 15.2 g. (0.200 mole) and 35.2 g. (0.200 mole) of EOc4 were warmed in 5 ml. of nitromethane to effect solution. A quantity (100 ml.) of ethyl acetate was added to the solution and the mixture was cooled to 0° C. causing precipitation of crystalline platelets. The crystals were determined to be a 1:1 ammonium thiocyanate:EOc4 complex. This complex may be used to prepare episulfides from oxiranes in nonprotonic media by contacting the oxirane with the thiocyanate in such a medium.

EXAMPLE 41

Pyridinium Halide Complexes

A mixture of 17.6 g. (0.100 mole) of EOc4 and 3.95 g. (0.050 mole) of pyridine was added to a 48% aqueous solution containing 8.4 g. (0.050 mole) of hydrogen bromide. Crystals were formed which were filtered, washed and air dried. Analysis showed the crystals to be an anhydrous 1:2 pyridinium bromide:EOc4 complex.

In the attempted synthesis of other EOc4:salt complexes, it was found that complexes are not formed with salts of all metals. Successful complexation only is noted herein.

We claim:

1. A composition of matter comprising a complex between:
    a. a cyclic tetramer represented by the formula $(CH_2CH_2O)_4$ and
    b. a salt of a pyridinium cation.

2. The composition of claim 1 wherein (b) is pyridinium bromide and the mole ratio of (b) : (a) is about 1:2.

* * * * *